United States Patent [19]

Cooper

[11] Patent Number: 5,205,155

[45] Date of Patent: Apr. 27, 1993

[54] AIR MONITORING CASSETTE

[75] Inventor: Patrick H. Cooper, North Charleston, S.C.

[73] Assignee: Envirometrics, Inc., Charleston, S.C.

[21] Appl. No.: 676,323

[22] Filed: Mar. 28, 1991

[51] Int. Cl.$^5$ ..................... B01D 27/08; B01D 35/30; G01N 1/00

[52] U.S. Cl. ................................ 73/28.04; 73/863.23; 73/863.25; 55/270

[58] Field of Search ................. 73/28.01, 28.04, 28.06, 73/31.03, 863.23, 863.25; 55/270

[56] References Cited

U.S. PATENT DOCUMENTS

| | | | |
|---|---|---|---|
| 3,679,973 | 7/1972 | Smith, Jr. et al. | 324/71 |
| 3,748,905 | 7/1973 | Fletcher et al. | 73/863.25 |
| 3,966,439 | 6/1976 | Vennos | 73/863.22 |
| 4,046,593 | 9/1977 | Au et al. | 134/21 |
| 4,178,794 | 12/1979 | Jugle et al. | 73/863.25 |
| 4,249,655 | 2/1981 | Patureau et al. | 73/863.23 |
| 4,277,259 | 7/1981 | Rounbehler et al. | 422/88 X |
| 4,324,568 | 4/1982 | Wilcox et al. | 73/40.7 |
| 4,790,857 | 12/1988 | Miksch | 55/16 |

OTHER PUBLICATIONS

"Evaluation of Filter Cassettes for Airborne Asbestos Sampling", Kathleen Maguire, Masters Thesis, University of South Carolina, 1990.
Safety Environmental Control, Inc., Millipore 25 mm Air Analysis Cassettes brochure.
NIOSH Manual of Analytical Methods, Method 7400, Revision No. 3—May 15, 1989.
"Uniformity of Particle Deposition for Indoor Air Sampling Under Anisokinetic Conditions", by Fletcher, Steel, Beard, Wang and Gentry.
Asbestos, U.S. Department of Labor Occupational Safety and Health Administration Title 29 CFR Part 1926.58 (Effective Jul. 21, 1986).
Environmental Express "The Right Move" advertising brochure.
Gelman Sciences Product Data Sheet, 1990.
Industrial Ventilation, A Manual of Recommended Practice, published by the American Conference of Governmental Industrial Hygienists, Fourteenth Edition, 1976, pp. 9-17, 9-19, 4-12 and 4-6.
Costar/Nuclepore Brochure, "New Nuclepore Air Monitor Cassettes for EPA and NIOSH Methods", p. 60.
Millipore Brochure, "Workplace and Environmental Testing and Analysis", pp. 2 and 3.
Asbestos Analytics, Inc. brochure, "Air Monitoring Cassettes", p. 8.

Primary Examiner—Tom Noland
Assistant Examiner—Michael Brock
Attorney, Agent, or Firm—Dority & Manning

[57] ABSTRACT

An air monitoring cassette for monitoring airborne particulate wherein the cassette includes a housing defining an airway therethrough. The housing includes an outlet end for connection to a pump. The housing further includes an inlet end opposite the outlet end and a filter to collect particulate thereon intermediate said outlet end and inlet end. The inlet end includes an outwardly flared inside surface so that particulate laden air can be drawn through the cassette and non-uniform deposition of particulate on the filter reduced.

25 Claims, 2 Drawing Sheets

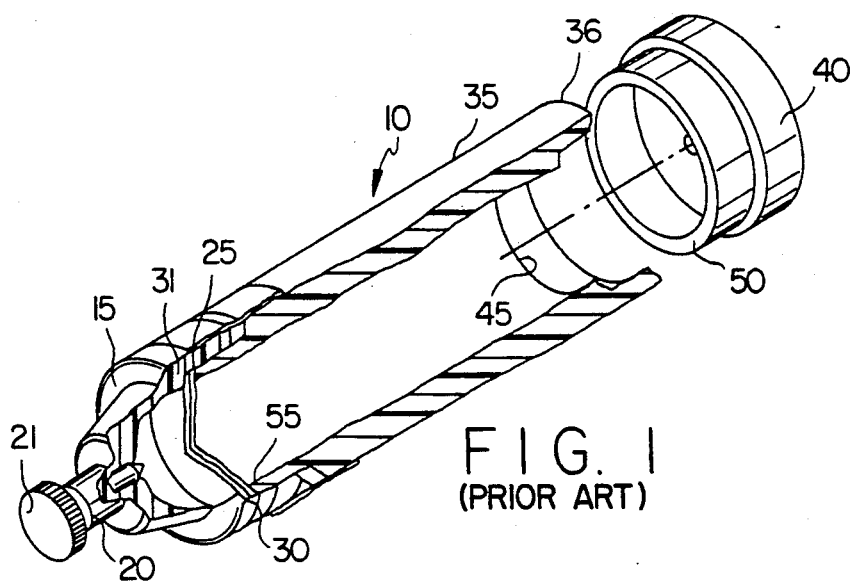
FIG. 1 (PRIOR ART)
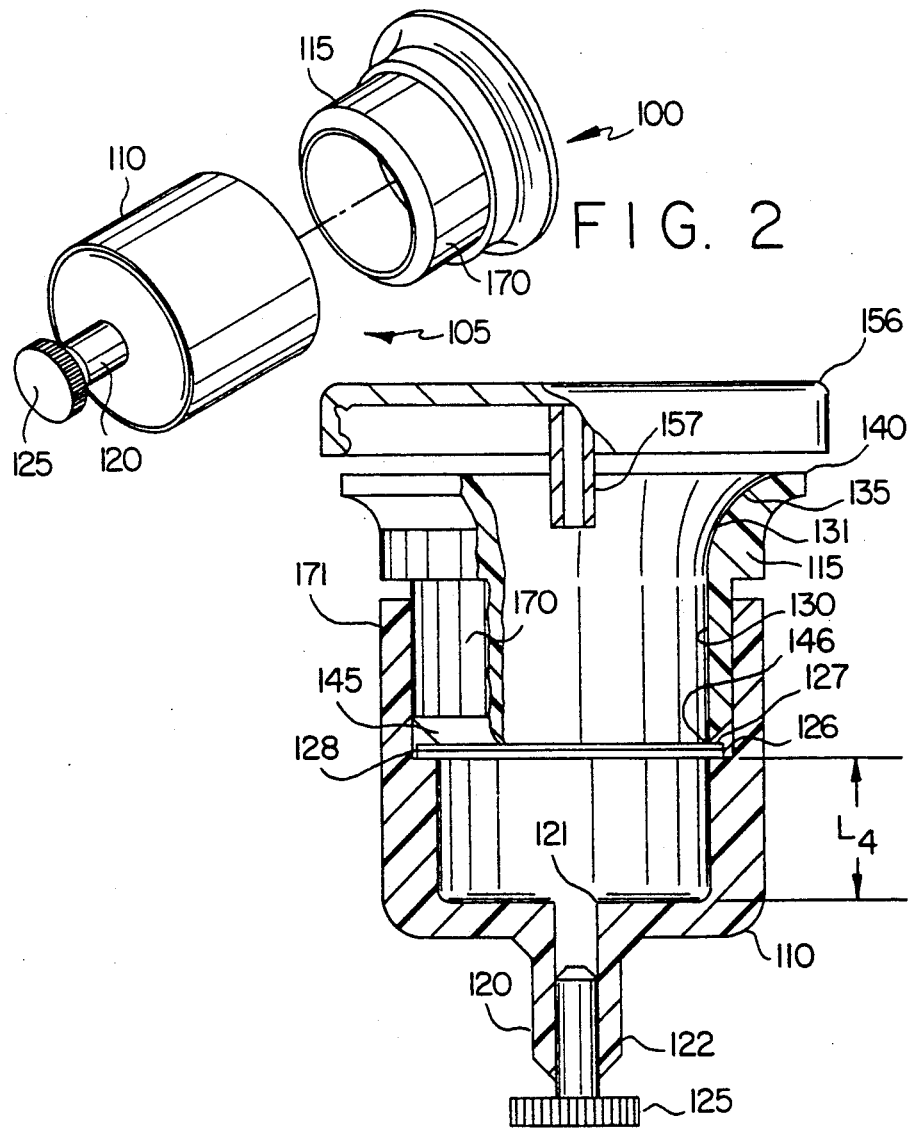
FIG. 2
FIG. 3

AIR MONITORING CASSETTE

BACKGROUND OF THE INVENTION

The present invention relates generally to monitoring devices, and more particularly to a novel bell mouth monitoring cassette for monitoring airborne particulate such as asbestos fibers and the like.

Recognition of the dangers of asbestos and the need for its measurement and control developed in the 1930's. Early methods of measuring airborne concentrations were based on the collection process of impingement in water. The collected particles in liquid suspension were then counted microscopically. With this method, all visible particles, fibrous and nonfibrous, were counted. This method was nonspecific as to the makeup of the particulate sampled and did not distinguish between the fibrous and nonfibrous component of the collected dust. This impinger method became the standard dust sampling instrument in the 1930's and was the first basis for the first standards for asbestos dust in the United States.

Through the years, many methods of measuring airborne particulate such as asbestos have been used. Based on the data developed, the National Institute for Occupational Safety and Health (NIOSH) concluded that measurement of the fibrous component of the dust was more appropriate for characterizing workplace atmospheres relative to the health hazard from asbestos exposure. NIOSH further concluded that the best index of asbestos exposure was the concentration of fibers longer than 5 $\mu$m collected on membrane filters, such fibers being counted using phase contrast microscopy.

The first version of the membrane filter procedure for monitoring airborne asbestos was published by NIOSH in 1968. After years of study and refinement, NIOSH published a formal method in 1976. This standardized method was developed and adopted to better control the sources of variability in the procedure, and improve the accuracy and the precision of the data collected. The procedure specified particulate collection on a 37 mm diameter mixed cellulose ester filter mounted in an open face plastic filter holder.

As the levels of acceptable exposure to asbestos were lowered, investigation continued concerning ways to reduce the variability of the results and improve the capability for measuring lower levels of airborne asbestos. A modification of the sampling device that proved effective involved use of a smaller filter, 25 mm in diameter. This, in effect, concentrated the sample in a smaller area thereby increasing the sensitivity of the analytical method.

In 1984, NIOSH issued a new sampling and analytical procedure (Method 7400) that utilized the 25 mm cassette. Later a protective 50 mm extension cowl was added to the open-faced holder. However, electrostatic effects introduced by this cowl caused a more non-uniform deposition of fibers on the filter. Since only a fraction of the filter is actually analyzed, any variability in this distribution of fibers on the filter vastly increases the variability of the estimation of the total number of fibers on the entire filter, and therefore causes an underestimation of airborne asbestos fiber concentration. To minimize this, an electrically conductive cowl was introduced in an attempt to minimize the electrostatic effect and produce a more uniform fiber distribution.

Through the years, government regulations have continuously lowered the level of acceptable exposure to airborne asbestos fiber. Thus, better control of the accuracy and variability of the monitoring procedure has become more and more important. Since the variability of the procedure increases drastically as the number of fibers counted decreases, reliable determination of these lower levels has been difficult and problematic.

Fiber distribution on the filter is a main factor contributing to the overall procedure variability. A key to improving the procedure is reducing non-uniform deposition of the fibers on the filter. Even with the electrically conductive cowl, non-uniform fiber deposition has remained a major source of variability in the procedure.

Currently, NIOSH, the Occupation Safety and Health Administration (OSHA), and the Environmental Protection Agency (EPA) have published procedures for sampling and analysis of airborne asbestos fibers. The sampling technique for these procedures generally involves drawing an accurately known volume of air through a membrane filter which is held in a cassette. A portion of the filter is then analyzed for determination of the number of fibers retained on the surface of the filter.

One method of analysis of the filter utilizes phase contrast microscopy to count all fibers meeting specified dimensional characteristics. Other methods have also been developed utilizing the more sophisticated technique of electron microscopy. While the electron microscope has the ability to differentiate asbestos particles from non-asbestos particles, it utilizes a smaller area of the filter for examination as compared to the phase contrast microscopy. Therefore, the actual part of the filter analyzed is even less representative of the total filter and minimizing non-uniform fiber deposition on the filter becomes even more important.

SUMMARY OF THE INVENTION

The present invention recognizes and addresses the foregoing disadvantages, and others, of air monitoring cassettes. Accordingly, it is an object of the present invention to provide an improved air monitoring cassette for monitoring particulate such as asbestos and the like.

It is another object of the present invention to provide an air monitoring cassette that reduces non-uniform deposition of particulate fibers on the filter.

It is another object of the present invention to provide a bell mouth adapter for use with air monitoring cassettes.

It is a further object of the present invention to provide a method of obtaining particulate samples that reduces non-uniform deposition of particulate on the filter.

It is still a further object of the present invention to provide an air monitoring cassette that enhances currently known monitoring techniques.

These and other objects are achieved by providing an air monitoring cassette for monitoring airborne particulate wherein the cassette comprises a housing defining an airway therethrough. The housing includes an outlet end adapted for connection to a means for drawing air through the housing. The housing further includes an inlet end opposite the outlet end and a filter adapted to collect particulate thereon intermediate said outlet end and inlet end, the inlet end including means for reducing non-uniform particulate deposition on the filter.

Generally, the invention is also embodied by providing an air monitoring cassette for monitoring airborne particulate wherein the cassette comprises a housing defining an airway therethrough. The housing includes an outlet end adapted for connection to a means for drawing air through the housing. The housing further includes an inlet end opposite the outlet end, the inlet end having an outwardly flared inside surface. The cassette also includes a filter adapted to collect particulate thereon, the filter located within the housing intermediate the outlet end and the inlet end whereby particulate laden air can be drawn through the cassette and particulate deposited on the filter.

In addition, the inlet end may include a first and second portion, the first portion defined by a substantially cylindrical inside surface and the second portion defined by an outwardly flared inside surface. Further, the diameter at the outermost end of the second portion may be greater than the distance between the outermost end of the second portion and the filter.

In addition, these and other object are also achieved by providing an inlet adapter for an air monitoring cassette with a housing defining an airway therethrough and a filter therein located intermediate an inlet end and an outlet end for collecting particulate thereon from particulate laden air drawn through the cassette, wherein the adapter comprises a first portion adapted to be connected to the inlet end of the cassette. The first portion includes a substantially cylindrical inside surface. The adapter also includes a second portion adjacent the first portion and defined by an outwardly flared inside surface whereby the adapter reduces turbulence of air drawn through the cassette.

These and other objects are also achieved by providing a method of obtaining samples of airborne particulate for analysis, the method comprising the steps of providing a housing with a filter therein, the filter being located between an air outlet portion and a flared air inlet portion, the diameter of the outermost portion of the flared air inlet portion being greater than the distance between the outermost portion and the filter. Further steps include locating the housing in a particulate laden environment, and directing particulate laden air through said housing and filter to enhance uniform deposition of particulate on the filter by drawing air in through the flared air inlet portion.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures, in which:

FIG. 1 is a perspective view of a prior art monitoring cassette;

FIG. 2 is a perspective view of an air monitoring cassette of the present invention;

FIG. 3 is a sectional view of the air monitoring cassette of FIG. 2 and including a cover that is removed during use;

Figure 4:
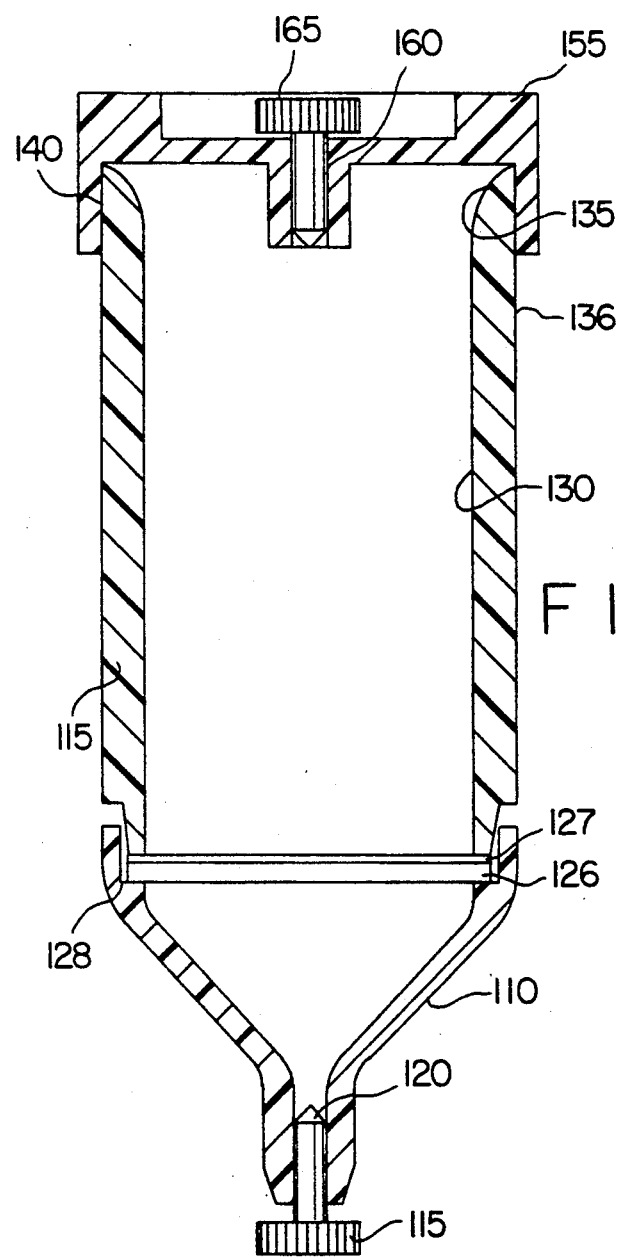
FIG. 4 is a sectional view of another embodiment an air monitoring cassette of the present invention.

Repeat use of reference characters in the present specification and drawings is intended to represent same or analogous features or elements of the invention.

DETAILED DESCRIPTION OF PREFERRED EMBODIMENTS

It is to be understood by those of ordinary skill in the art that the present discussion is a description of exemplary embodiments only, and is not intended as limiting the broader aspects of the present invention, which broader aspects are embodied in the exemplary constructions.

Referring to FIG. 1, a prior art air monitoring cassette is illustrated generally at 10. The cassette includes a base portion 15 with an outlet 20 adapted to be connected to a pump or the like for drawing air through the cassette. The outlet 20 includes a plug 21 for closing the outlet. The base portion 15 includes a filter 25 supported on a pad 30 which is supported on a ledge 31. The base portion 15 tapers inwardly between the ledge 31 and the outlet 20. The cassette further includes a 50 mm extension cowl 35 removably attached to the base portion 15 and a cover 40 for covering the open end of the cowl. The outer portion 36 of extension cowl 35 includes a ledge 45 that is adapted to engage with the inner portion 50 of the cover when the cover is on to facilitate removal of the cover for use. The cover may also include an air passage therethrough so that the cassette can be calibrated.

The inner portion of the cowl 35 includes a portion 55 adapted to contact the filter 25 when the cowl is in place. In use, cover 40 is removed and air is drawn in through the extension cowl through the filter 25 and out the outlet 20. After a predetermined volume of air has been drawn therethrough, the filter is removed and analyzed to determine the number of asbestos fibers on a given portion of the filter.

FIGS. 2-5 illustrate a preferred embodiment of a cassette in accordance with the present invention. Referring to FIG. 2, a bell mouth air monitoring cassette is illustrated generally at 100. The cassette comprises a housing generally illustrated at 105 that defines an airway therethrough. The housing 105 includes an outlet end 110 and an inlet end 115, with the outlet end and inlet end preferably comprising two separable, but matable, pieces. A protective tape (not shown) may be jointly secured to the outlet end and the inlet end to ensure the integrity of the sample as is readily apparent to those skilled in the art. As best illustrated in FIG. 3, the outlet end 110 includes a portion 120 adapted for connection to a means for drawing air through the housing. As embodied herein, the means for drawing air through the housing can be a conventional pump or negative pressure device as would be readily apparent to one of ordinary skill in the art. As illustrated in FIG. 3, portion 120 includes a first section 121 where air enters 120 and a second section 122 where air exits 120. A plug 125 is provided for portion 122 when not in use to prevent air or contaminates from entering the housing.

As best illustrated in FIG. 3, the cassette includes a support pad 126 and a filter 127. The filter is adapted to collect particulate such as asbestos fibers thereon and is located intermediate the outlet end 110 and the inlet end 115. In a preferred embodiment, the filter is maintained on the pad 126 and supported on ledge 128 in the housing 105. In a preferred embodiment, as illustrated in FIG. 3, the interior of the outlet end between the ledge 128 and first section 121 is defined by a continuous cylindrical surface of constant diameter. Such surface is preferably smooth and uninterrupted. In addition, the distance L4 between the ledge where the filter is supported and section 121 of portion 120 is approximately 0.3 inches.

In a preferred embodiment for use in asbestos monitoring, the filter comprises a mixed ester of cellulose membrane approximately 0.006 inch thick with a pore size between 0.45 $\mu$m and 1.2 $\mu$m and the pad is comprised of 100% cellulose fiber approximately 0.035 inch thick. Of course, the type and dimensions of the filter and pad depend on the particulate being monitored and selection of such for a particular environment is well within the capabilities of one of ordinary skill in the art.

As illustrated in FIGS. 2 and 3, inlet end 115 is located opposite outlet end 110. Inlet end 115 includes means for reducing non-uniform deposition of particulate on the filter. As embodied herein, the means for reducing non-uniform deposition of particulate on the filter includes an outwardly flared inside surface 135 on the inlet end. In a preferred embodiment, the inlet end includes a first portion 130 that has a substantially cylindrical inside surface and a second portion 131 that includes outwardly flared inside surface 135. The outwardly flared inside surface 135 is arcuate and smooth. The inlet end includes an outermost end 140 and an innermost end 145. The innermost end 145 includes an angled portion 146 that contacts the filter 127 around its circumference. It is preferred that the housing provide a smooth surface between the area air enters (around 140) and the filter to reduce turbulence of the air in the housing and non-uniform fiber deposition on the filter. It is also preferred that this smooth surface be continuous and not interrupted in any manner that might prevent fibers in the air from reaching the filter.

In a preferred embodiment, the inlet end comprises a bell-mouth as illustrated in FIG. 3, but it is not necessary that the outer surface of the inlet be flared. Bell-mouth, as embodied herein is understood to describe an inlet where at least a portion of the inner surface flares outwardly as illustrated in FIG. 3. In a preferred embodiment, the bell mouth includes a portion 170 with an outer diameter dimension so as to be received within portion 171 of the outlet end 110.

Figure 5:
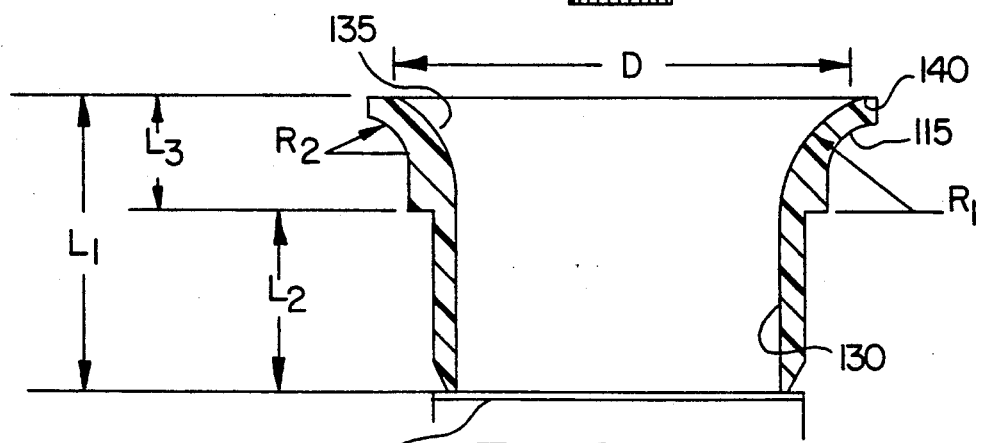
FIG. 5 is a sectional view of the inlet portion of FIG. 2.

In a most preferred embodiment, as illustrated in FIGS. 3 and 5, the diameter D of the outermost end 140 of the second portion 135 is greater than the distance L1 between the outermost end 140 of the second portion 135 and the filter 127. In a most preferred embodiment for asbestos monitoring, the filter is approximately 25 mm in diameter and the diameter D of the outermost portion 140 of the outwardly flared inside surface is approximately 1.251 inches. In addition, the distance L1 between the outermost portion of the inlet end and the filter is approximately 0.681 inch (17.3 mm). Further, the length L2 of the first portion is approximately 0.381 inches. The length L3 of radius R1 is approximately 0.30 inches. Further, in a most preferred embodiment, radius R1 is approximately 0.332 inch and radius R2 is approximately 0.1785 inch. Radius R1 should be smooth and continuous. It should be understood that these dimensions are representative of a preferred embodiment and should not be construed as restrictive of the invention.

Another preferred embodiment of the present invention is illustrated in FIG. 4. As embodied in FIG. 4, inner surface 135 is flared and outer surface 136 is straight. Further, FIG. 4 illustrates an embodiment where the outwardly flared inner surface 135 is integral with an extended first portion 130. The embodiment of FIG. 4 also includes an outlet end 110 and a filter 127 and pad 126. The pad and filter are supported on ledge 128.

The cassette 100 also includes a calibration cover 155 as illustrated in FIG. 4. Calibration cover 155 is adapted to extend over the inlet end 140 of the cassette. Calibration cover 155 includes an air passage 160 therethrough and a plug 165. To calibrate the cassette, air can be drawn through the housing by passing air from passage 160 to passage 120. In addition, the cassette can also include a cover as illustrated at 156 in FIG. 3. Such a cover would prevent contamination of the cassette prior to use and provide sample protection after collection. In use, the covers 155 or 156 are removed. Covers 155 and 156 can be interchangeably used with the various embodiments, that is as illustrated in FIG. 3 or FIG. 4. Furthermore, cover 156 includes a protrusion 157 so that the cover can be placed on a support surface with the protrusion 157 extending upwardly and the portion 120 of the housing can receive the protrusion therein. Therefore, the cover can serve as a support for maintaining the cassette upright for analysis or other purposes.

In another preferred embodiment of the present invention inlet end 115 as illustrated in FIGS. 2, 3 and 5 can be used as an adapter for a conventional air monitoring cassette such as the one illustrated in FIG. 1. As described above, a conventional cassette includes a 50 mm extension cowl with a ledge 45 (FIG. 1) near its outer end. In a preferred embodiment, the adapter of the present invention includes a first portion 130 adapted to be connected to the inlet end of a cassette such as 36 in FIG. 1. The first portion may include a substantially cylindrical inside surface such as illustrated in FIGS. 3 and 5 at 130, but such is not essential. The adapter also includes a second portion 135 adjacent the first portion and defined by an outwardly flared inside surface as illustrated at 135 in FIGS. 3 and 5. As illustrated, the first and second portions are preferably unitary. The first portion 130 includes a section 170 (FIG. 2) that is adapted to matingly engage the extension cowl 35 and abut on its end with ledge 45 to provide a substantially smooth inside surface from the outermost end 140 of inlet end 115 to the filter 25. This provides for reduced turbulence of the air entering the cassette as well as eliminates ledge 45 from being a non-smooth surface that interferes with the particulate entering the housing. Since the fibers or particulate are being transported in the air drawn through the cassette, providing a smooth surface from the inlet end to the filter prevents fibers and the like from becoming entrapped on the ledge and not proceeding to the filter.

Another preferred form of the invention resides in providing a method of obtaining samples of airborne particulate for analysis comprising the steps of (a) providing a housing with a filter therein located between an air outlet portion and a flared air inlet portion, (b) locating the housing in an environment with particulate laden air, and (c) directing particulate laden air through the housing and filter to enhance uniform deposition of particulate on the filter by drawing air in through the flared inlet portion. In one preferred embodiment of the method, the diameter of the outermost portion of the flared air inlet portion is greater than the distance between the outermost portion and the filter. The method further includes the step of removing the filter from the housing for analysis.

In a preferred embodiment the cassette is constructed from electrically conductive polypropylene plastic, but non-conductive plastic could also be used. In addition, any other material that would perform in a similar manner could be utilized for the cassette. Further, it is within the scope of this invention to monitor any type airborne particulate such as, for example, other type fibers, airborne microorganisms or the like.

These and other modifications and variations to the present invention may be practiced by those of ordinary skill in the art, without departing from the spirit and scope of the present invention, which is more particularly set forth in the appended claims. The various elements set forth in different embodiments herewith, are interchangeable both in whole or in part. Furthermore, those of ordinary skill in the art will appreciate that the foregoing description is by way of example only, and is not intended to be limitative of the invention so further described in such appended claims.

With regard to the present invention, laboratory investigation has been conducted comparing nine 25 mm sampling cassettes with respect to radial fiber distribution on the filters. The first seven tested were commercially available cassettes that included extended cowls similar to that illustrated in FIG. 1. In addition, a cassette with an extended cowl and a bell mouth adapter or attachment was tested, and a cassette substantially as embodied in FIG. 2 was tested.

The tests indicated that the cassettes with the bell mouth inlets reduced non-uniform deposition of particulate as compared to the first seven cassettes tested. In addition, the tests showed that the cassette substantially as embodied in FIG. 2 provided the best results.

What is claimed is:

1. An air monitoring cassette for monitoring airborne particulate, said cassette comprising:
   a housing defining an airway therethrough, said housing including an outlet end adapted for connection to a means for drawing air through the housing;
   said housing further including an inlet end opposite said outlet end, said inlet end having an outwardly flared inside surface; and
   a filter adapted to collect particulate thereon, said filter located within said housing intermediate said outlet end and said inlet end so that particulate laden air can be drawn through said cassette and particulate deposited on the filter.

2. An air monitoring cassette as in claim 1, wherein said inlet end is separable from said housing.

3. An air monitoring cassette as in claim 1, wherein said housing has a smooth inner surface between the inlet end and the filter.

4. An air monitoring cassette as in claim 1, wherein said inlet end includes a first portion defined by a substantially cylindrical inside surface and a second portion defined by an outwardly flared inside surface.

5. An air monitoring cassette as in claim 4, wherein the diameter of the outermost end of the second portion is greater than the distance between the outermost end of the second portion and the filter.

6. An air monitoring cassette as in claim 1, and further including a removable cap adapted to be secured to the inlet end as a cover and including a protrusion adapted to be received in said outlet end for supporting the cassette in an upright position after use.

7. An air monitoring cassette as in claim 1, wherein said inlet end is bell mouthed.

8. An air monitoring cassette as in claim 1, wherein the diameter of the outermost portion of the outwardly flared inside surface is approximately 1.251 inches.

9. An air monitoring cassette as in claim 1, wherein the distance between the outmost portion of the inlet end and the filter is approximately 0.681 inches.

10. An air monitoring cassette as in claim 1, wherein said particulate comprises asbestos fibers.

11. An air monitoring cassette as in claim 1, wherein said housing includes a ledge therein for supporting the filter and said outlet end includes a continuous cylindrical surface of constant diameter between the ledge and an innermost portion of the end adapted for connection to the means for drawing air through the housing.

12. An air monitoring cassette for monitoring airborne particulate, said cassette comprising:
    a housing defining an airway therethrough, said housing including an outlet end adapted for connection to means for drawing air therethrough;
    said housing further including an inlet end opposite said outlet end and a filter adapted to collect particulate thereon intermediate said outlet end and inlet end;
    said inlet end including means for reducing non-uniform deposition of particulate on the filter; and
    wherein said means for reducing non-uniform deposition of particulate includes an outwardly flared inner surface at the end of the inlet end where air enters the cassette.

13. An air monitoring cassette as in claim 12, wherein said means for reducing non-uniform deposition of particulate includes a first portion defined by a substantially cylindrical inside surface and a second portion defined by an outwardly flared inside surface.

14. An air monitoring cassette as in claim 13, wherein at least part of said first portion contacts said filter.

15. An air monitoring cassette as in claim 12, wherein said outlet end and inlet end are separable.

16. An air monitoring cassette for monitoring airborne asbestos fibers, said cassette comprising:
    a housing with a cylindrical inside surface and defining an airway therethrough and including a ledge therein for supporting a filter, said housing further including an outlet end, said outlet end including an inner portion and an outer portion, said outer portion adapted for connection to a means for drawing air therethrough;
    the interior of the outlet end between the ledge and the inner portion of the outlet end being defined by a continuous cylindrical surface of constant diameter;
    said housing further including an inlet end opposite said outlet end, said inlet end including a bell mouth entry portion for reducing turbulence of the air drawn through the cassette, said bell mouth entry portion defining a smooth continuous inside surface; and
    a filter adapted to collect asbestos fibers thereon, said filter located within said housing on said ledge intermediate said outlet end and said inlet end.

17. An air monitoring cassette as in claim 16, wherein said inlet end is separable from said housing.

18. An air monitoring cassette as in claim 16, wherein said bell mouth entry portion has a flared inner surface with a radius of approximately 0.332 inches.

19. An air monitoring cassette for monitoring airborne particulate, said cassette comprising:

a housing defining an airway therethrough, said housing including an outlet end adapted for connection to a means for drawing air through the housing;

said housing further including an inlet end opposite said outlet end, said inlet end having a first portion defined by a substantially cylindrical inside surface and a second portion defined by an outwardly flared inside surface; and a filter adapted to collect particulate thereon, said filter located within said housing intermediate said first portion and said outlet end whereby particulate laden air can be drawn through said cassette and non-uniform deposition of particulate on the filter reduced.

20. An air monitoring cassette as in claim 19, wherein said inlet end is separable from said outlet end.

21. An inlet adapter for an air monitoring cassette with a housing defining an airway therethrough and a filter therein located intermediate an inlet end and an outlet end for collecting particulate thereon from particulate laden air drawn through the cassette, said adapter comprising:

a first portion adapted to be connected to said inlet end of said cassette, said first portion including a substantially cylindrical inside surface; and a second portion adjacent said first portion and defined by an outwardly flared inside surface whereby said adapter reduces turbulence of air drawn through the cassette.

22. An adapter as in claim 21, wherein said first and second portions are unitary.

23. An air monitoring cassette for monitoring airborne particulate, said cassette comprising:

a housing defining an airway therethrough, said housing including an outlet end adapted for connection to a means for drawing air through the housing;

said housing further including an inlet end opposite said outlet end, said inlet end being outwardly flared and terminating at an outermost portion; and a filter adapted to collect particulate thereon, said filter located within said housing intermediate said outlet end and said inlet end; and the diameter of the outermost portion of the inlet end being greater than the distance between the outermost portion of the inlet end and the filter, whereby particulate laden air can be drawn through said cassette and non-uniform deposition of particulate on the filter reduced.

24. A method of obtaining samples of airborne particulate for analysis, said method comprising the steps of:

a) providing a housing with a filter therein, said filter being located between an air outlet portion and a flared air inlet portion, the diameter of the outermost portion of the flared air inlet portion being greater than the distance between the outermost portion and the filter;

b) locating the housing in an environment with particulate laden air; and c) directing particulate laden air through said housing and filter to enhance uniform deposition of particulate on the filter by drawing air in through the flared air inlet portion.

25. The method of obtaining samples as set forth in claim 24, and further comprising the step of removing the filter from the housing for analysis.

* * * * *